(12) United States Patent
Flaction

(10) Patent No.: US 10,391,360 B2
(45) Date of Patent: Aug. 27, 2019

(54) METHOD AND DEVICE FOR OPTIMIZING THE TRAINING OF ATHLETES

(75) Inventor: Patrick Flaction, Chandolin-Pres-Saviese (CH)

(73) Assignee: Myotest SA, Scion (CH)

(*) Notice: Subject to any disclaimer, the term of this patent is extended or adjusted under 35 U.S.C. 154(b) by 501 days.

(21) Appl. No.: 12/485,178

(22) Filed: Jun. 16, 2009

(65) Prior Publication Data

US 2010/0317489 A1    Dec. 16, 2010

(51) Int. Cl.
*A61B 5/22* (2006.01)
*A63B 24/00* (2006.01)
*A61B 5/11* (2006.01)

(52) U.S. Cl.
CPC ...... *A63B 24/0062* (2013.01); *A63B 24/0075* (2013.01); *A61B 5/11* (2013.01); *A61B 5/1122* (2013.01); *A61B 5/224* (2013.01); *A61B 2503/10* (2013.01); *A61B 2562/0219* (2013.01); *A63B 2220/17* (2013.01); *A63B 2220/40* (2013.01)

(58) Field of Classification Search
CPC . A61B 5/1122; A61B 5/11; A61B 2562/0219; A61B 5/224; A61B 2503/10; A61B 2220/40; A61B 2220/17; A61B 24/0075; A61B 24/0062; A63B 24/0062; A63B 2024/0065; A63B 2024/0068; A63B 24/0075; A63B 2024/0081; A63B 2220/40; A63B 2220/30; A63B 2220/50; A63B 2220/51; A63B 23/0244; A63B 2220/00; A63B 2220/62; A63B 2220/64

USPC .................................................... 482/1, 8–9
See application file for complete search history.

(56) References Cited

U.S. PATENT DOCUMENTS

| | | | |
|---|---|---|---|
| 4,699,379 A | 10/1987 | Chateau et al. | |
| 4,824,103 A | 4/1989 | Smidt | |
| 5,056,783 A | 10/1991 | Matcovich et al. | |
| 5,184,295 A * | 2/1993 | Mann | 473/221 |
| 5,474,083 A | 12/1995 | Church et al. | |
| 5,476,103 A | 12/1995 | Nahsner | |
| 5,738,616 A * | 4/1998 | Robertson | 482/102 |
| 5,788,655 A | 8/1998 | Yoshimura et al. | |
| 5,931,763 A * | 8/1999 | Alessandri | 482/4 |
| 6,148,280 A | 11/2000 | Kramer | |
| 6,231,481 B1 | 5/2001 | Brock | |
| 6,234,975 B1 | 5/2001 | McLeod et al. | |
| 6,397,151 B1 | 5/2002 | Yamagishi et al. | |

(Continued)

FOREIGN PATENT DOCUMENTS

| | | |
|---|---|---|
| CN | 2930773 Y | 8/2007 |
| DE | 4426302 | 2/1996 |

(Continued)

*Primary Examiner* — Loan B Jimenez
*Assistant Examiner* — Shila Jalalzadeh Abyaneh
(74) *Attorney, Agent, or Firm* — Blank Rome LLP

(57) ABSTRACT

A method for optimizing the training of athletes, including the steps of during a test, measuring with a portable device (1) a series of acceleration values during a series of N short movements performed by the athlete. Then, calculating with the device a plurality of muscular parameters based on the series of acceleration values. The device then determines a set of training exercises personalized for the athlete, based on the muscular parameters and presents the said set of training exercises to the athlete. The device then verifies the execution of the training exercises.

23 Claims, 11 Drawing Sheets

(56) References Cited

U.S. PATENT DOCUMENTS

| | | | |
|---|---|---|---|
| 6,635,013 B2 * | 10/2003 | Pfeffer | A63B 22/00 |
| | | | 128/920 |
| 2002/0028730 A1 * | 3/2002 | Kaufman | 482/8 |
| 2002/0170193 A1 | 11/2002 | Townsend et al. | |
| 2003/0027118 A1 * | 2/2003 | Abraham-Fuchs et al. | 434/258 |
| 2004/0134274 A1 | 7/2004 | Hoggan et al. | |
| 2005/0075586 A1 | 4/2005 | Jamsen | |
| 2005/0172311 A1 | 8/2005 | Hjelt et al. | |
| 2006/0025282 A1 * | 2/2006 | Redmann | A61B 5/103 |
| | | | 482/8 |
| 2006/0191335 A1 | 8/2006 | Nose et al. | |
| 2006/0253210 A1 * | 11/2006 | Rosenberg | G11B 27/005 |
| | | | 700/94 |
| 2007/0027369 A1 | 2/2007 | Pagnacco et al. | |
| 2007/0042866 A1 | 2/2007 | Skilken et al. | |
| 2007/0172797 A1 * | 7/2007 | Hada | G09B 23/32 |
| | | | 434/1 |
| 2009/0062627 A1 * | 3/2009 | Younger | A63B 24/0003 |
| | | | 600/301 |
| 2009/0069722 A1 * | 3/2009 | Flaction et al. | 600/587 |
| 2009/0150113 A1 * | 6/2009 | Kim et al. | 702/127 |
| 2010/0179027 A1 * | 7/2010 | McGlynn | A63B 24/0075 |
| | | | 482/9 |

FOREIGN PATENT DOCUMENTS

| | | | |
|---|---|---|---|
| DE | 102004013399 | 10/2005 | |
| EP | 1834583 A1 * | 9/2007 | A61B 5/22 |
| GB | 2422790 A | 8/2006 | |
| GB | 2447915 | 10/2008 | |
| JP | H04197280 A | 7/1992 | |
| JP | 2006320533 A | 11/2006 | |
| WO | WO03032826 | 4/2003 | |
| WO | 2005055815 A2 | 6/2005 | |
| WO | WO2005074795 | 8/2005 | |
| WO | WO2007036611 | 4/2007 | |
| WO | WO2007/107491 | 9/2007 | |
| WO | WO 2007107491 A1 * | 9/2007 | A61B 5/224 |
| WO | WO2009024600 | 2/2009 | |

\* cited by examiner

METHOD AND DEVICE FOR OPTIMIZING THE TRAINING OF ATHLETES

The present invention relates to the field of methods and devices for optimizing the training of athletes, especially for sport and for rehabilitation. The present invention relates in particular to methods and devices for evaluating muscular physiological parameters, for example muscular power and force, and for preparing and following up personalized training programs based on those test results. More generally, the present invention relates to the use of accelerometers for preparing personalized training programs.

PRIOR ART

Performance measurement apparatus is being increasingly used for the training of athletes and for rehabilitation after an accident. For example in cardiovascular training (jogging, cycling, etc.), the use of heartbeat meters ("pulsometers") and pedometers has grown substantially in recent years. Such portable apparatus takes measurements during exertion, enabling the athlete to adapt the training using objective data. The measured quantities delivered typically indicate the heartbeat rate, the distance traveled, the duration of training, the average or maximum speed, etc. However, they do not provide any direct measurement of the muscular power of the athlete or of a muscular chain of the athlete.

U.S. Pat. No. 5,788,655 (Omron) describes an apparatus intended to be fixed to the body and provided with an accelerometer and an LCD display. The apparatus permanently measures the movements of the wearer in order to determine his level of physical activity and other metabolism-dependent quantities, for example the daily calorie consumption of the user. This type of apparatus is useful for measuring the level of sedentariness of patients more objectively. However, it is unsuitable for muscular training and for measuring brief exertions, and is unable to determine for example the maximum power of an athlete's muscle group.

WO2005/074795 (Nokia) describes a measurement terminal provided with an accelerometer, the terminal being attached to the body of an athlete. The measurement data is evaluated so as to provide a quantity representative of the intensity of exertion delivered. Again, the objective is to determine the level of activity over a long period, for example a day or a week.

WO03/032826 (Philips) describes a similar system, provided with a three-axis accelerometer for determining the level of physical activity of a patient. The proposed device displays quantities such as the daily metabolic rate, the daily energy expenditure or the energy expenditure induced by exercise. This apparatus is therefore useful for measuring accelerations over a period of several hours, or even several days.

The devices of the type described above are therefore suitable essentially for measuring activity during lengthy exercising, for example over the course of a jogging session, a badminton match or an ordinary day. There are also quite similar devices for detecting falls by the aged, the time that they spend sitting down, standing up or lying down, etc. Accelerometers based devices for measuring and calculating the length of a path run by a jogger, the amount of calories burnt, etc, are also well known in the prior art.

Those devices are generally intended for measuring and determining parameters based on series of accelerations values measured over a training session of, typically, at least ten minutes or more. During such a session, the athlete, for example a runner or biker, often does not make any single move at maximal speed or maximal force. Even if he does so, the device does not know when he does. Those devices are thus only poorly adapted for determining basic muscular parameters of the athlete, such as the force of the athlete's legs, or the maximal speed at which the athlete can move his legs, which can only be retrieved from short tests performed at maximal speed of force, like simple jumps or lifts for example. Moreover, those known devices do not provide any instruction or guidance to the athlete in order to explain to him the kind of short moves which are expected in order to determine muscular parameters. In most cases, the sampling frequency is just insufficient and does not allow enough measures during a short move.

It is well known however that even in endurance sports like running, biking, and sport teams for example, the performance does not depend only on cardiovascular training, but also significantly on force and on other muscular parameters. Even a marathon runner thus needs to be able to verify those muscular parameters, and to control the progress made with those parameters during his training.

Measurement devices specifically intended for training and for measurement of brief movements are known in the prior art. For example, U.S. Pat. No. 5,474,083 describes a system intended for monitoring weightlifting movements by a patient. The system employs electrodes for measuring the activity of the patient's muscles during the movement and also a weight movement detector. An alarm is triggered in the event of an inappropriate movement. This system is useful for preventing accidents caused by lifting weights incorrectly or for training people to lift weights without hurting themselves. However, it is inappropriate for measuring the muscular performance of a sportsman. Moreover, the use of electrodes makes it not very practical to use.

U.S. Pat. No. 6,397,151 describes a wristwatch device comprising an accelerometer for measuring a sequence of accelerations of the forearm during a blow in a martial arts sport. The force exerted is then calculated. The accelerometer measures an acceleration along a single axis, which must be perfectly aligned with the direction of movement of the forearm.

US2004/134274 describes a device for measuring muscular force.

Those devices do not provide any support for improving training programs.

U.S. Pat. No. 6,148,280 (Virtual Technologies) describes a device provided with accelerometers and gyroscopes placed over the entire body of an athlete. The data delivered by several sensors is transmitted to a personal computer, which enables the trajectory and other characteristics of the movement to be analyzed. This system is complex, as it employs several sensors, including expensive goniometers, which are relatively fragile. Connecting the sensors together and to the external computer makes the device expensive and awkward to install. It is suitable for precise movement training, for example a golf swing, but does not allow direct determination of the muscular capacity developed by the sportsman during this movement.

DE4426302 describes an accelerometer used in combat sports to measure the acceleration of the striking surface. The apparatus is not portable and is suitable only for combat sports, such as boxing, karate, etc. An external computer has to be employed in order for the measurement results to be evaluated and displayed.

WO2007107491, filed by the applicant, describes a device and a method for evaluating muscular physiological parameters of athletes using a short test, such as lifts and/or jumps, wherein a removable and electrically autonomous measurement device is fastened to a weight that moves during the test, said measurement device being based on a three-axis accelerometer. A sequence of successive accelerations of said weight is determined during the test; and immediately at the end of said test, at least one quantity representative of said muscular capacity, which is determined from said sequence of accelerations, is indicated on a display of the device.

This device is very useful for determining, with a series of short tests such as simple jumps, muscular parameters of any athlete, including the maximum force and speed for example. It is also suggested to transfer those results to an external device, such as a personal computer, from which a personalized training program can be computed and displayed. Computation of such a personalized program, for which there are no explanations in this patent document, thus requires an additional external device. Moreover, the device does not provide any help for verifying the correct execution of this personalized program by the athlete.

WO09024600, filed by the applicant, describes another accelerometer based device for measuring and computing muscular parameters with a series of short tests.

WO2007036611 discloses an evaluation method using an accelerometer for estimating the maximal weight a person is capable of lifting, based on short tests.

Other devices, including pulsemeters, are known that suggest to the athlete a personalized level of intensity for the training, for example a personalized range of pulse rate, based on previous measures. Those devices do not propose different exercises to different athletes, but only different intensities for the same exercise.

Other devices based on accelerometers and gyroscopes exist, enabling for example the trajectory of a golf swing to be monitored so as to improve the movement. U.S. Pat. No. 5,056,783 describes for example a baseball bat provided with a three-axis accelerometer in order to specify the movement of the bat in space. This type of device delivers a large amount of data, for example the position and speed of the sensor at each instant, often requiring a large screen or an external device to display this data. However, such devices are unable to calculate and display thereon one or more quantities representing the athlete's muscular capacity.

GB2447915A1 describes a computerised system consisting of a database and multimedia user interface that creates fitness training programs that are individualized for the athlete. An initial computerised electronic questionnaire is filled out to provide the athlete with a training program that is personalized to their needs and that of their sport and position. The system requires a form which is tedious to fill, and a computer which is usually not available in most fitness rooms.

CN2930773Y describes a treadmill which helps the user to formulate its training plan. This solution requires a treadmill, and is not adapted to other exercises.

DE102004013997A1 describes a method for an apparatus such as a training bike. Data such as pulse, blood pressure, respiration rate and stress condition, of a person exercising on the apparatus are determined. The data are recorded in a data medium e.g. CD, and transmitted to an attendant e.g. physiotherapist. The plan is revised by the attendant based on the received data. The revised plan is again transmitted to the apparatus.—This method thus requires manual intervention of a physiotherapist, and is only adapted to one specific exercise performed on one apparatus.

BRIEF SUMMARY OF THE INVENTION

There is therefore a need for a new method and device for testing and training muscular parameters of an athlete, in particular muscular parameters of endurance of athletes such as runner, biker, team sport athletes, etc.

According to the invention, these aims are achieved by means of a method for optimizing the training of athletes, comprising the steps of:

during a test, measuring with a portable device a series of acceleration values during a series of N short movements performed by the athlete;

calculating with said device a plurality of muscular parameters based on said series of acceleration values;

determining with said device a set of training exercises personalized for said athlete, based on said muscular parameters;

presenting said set of training exercises to said athlete with said device;

verifying with said device the execution of said training exercises.

This method provides the advantage, among other, of needing only a single device for testing and determining muscular parameters of the athlete, for providing a set of training exercises personalized for the athlete and depending on the measured muscular parameters, and for verifying the correct execution of the training exercises.

The short movements that the athlete needs to perform during the initial test typically include short vertical jumps, such a squat jumps and/or countermovement jumps, or other short tests useful for measuring muscular parameters of the legs and feet, among other.

The muscular parameters measured and computed during and immediately after this initial test preferably comprise: muscular force, extension (thrust speed), reactivity, muscular stiffness, coordination (or variation of the reactivity over several successive jumps), etc.

In a series of jumps, the reactivity is defined as the (flight time)$^2$/(time of contact with the ground), or as the average of the value between several successive jumps.

The coordination indicates the capacity of the athlete to control his muscle and to repeat successive jumps at the same pace, while absorbing chocks. In a preferred embodiment, the coordination is computed by normalizing the reactivity, in order to have an average reactivity over all the springs which is equal to 1. This normalization is necessary since it is more difficult to achieve a good coordination when the reactivity is high (when the athlete spends a higher time in the air) than with lower reactivity.

The coordination then depends on the residual sum of squares (ssresid), i.e., the sum of the squared differences between the actual values of each reactivity measure and the estimation line computed with the "least square methods". If the reactivity is the same for all the springs, the coordination is maximal; this coordination decreases when the average deviation increases.

It is believed that the measure and training of reactivity and coordination for improving the performance of endurance athletes, such as runner, is new. It is also believed that the use of a three-axis accelerometer for determining this coordination is entirely new.

Those parameters are preferably displayed in relative values, for example as a percentage of values reached by referenced athletes, for example top athletes, rather than (or in addition) with absolute values. This allows an athlete to immediately see the parameters which he needs to train in order to get values closer to the ones reached by referenced athletes.

The set of training exercises proposed by the device is automatically selected in order to improve the weakest parameters of the athlete. In one example, the device automatically determines a set of exercises depending on the two weakest muscular parameters of the athlete.

This set of exercise is preferably selected among a predefined catalogue of exercises. Each exercise is preferably identified by an identifier, such as a number, for easy retrieval of a description of the exercise in an associated manual, or on a support such as a DVD or web site for example.

The set of exercise preferably comprise a series of different short exercises, such as jumps, lifts, and other gymnastic exercises. The set of exercises may also comprise a personalized session of interval running, including periods of runs at various paces and short exercises between said periods. Both types of exercises may also be proposed, as alternatives or complements. The total duration of each type of exercise is much longer than the initial check; for example, the initial test of muscular parameters may be performed in less than 5 minutes, while a personalized training session would possibly last 30 minutes or more, and must be repeated to be effective.

The training with the prescribed exercises is preferably guided and verified with the device, which displays or otherwise gives to the athlete indications about the next exercise to do, the required pace for each exercise, etc, and also verifies if those instructions are correctly followed. Verification of the execution also preferably implies verification of accelerations values measured during this training.

The device may also be used during the training session for measuring some muscular parameters, and verifying the progress of the athlete. In one embodiment, the training session is adapted based on those measures.

The device is thus used for initial muscular tests, in order to determine the muscular parameters of an athlete at a given point of time, and during the training, using a training program computed by the device and depending on this initial test.

Parameters measured and computed during different sessions, for example on different days or weeks, are preferably stored within the device. Older sessions may be retrieved, displayed, and/or used for determining new training plans. The device may thus adapt the proposed training program to the progresses made by the athlete, detect overtraining, and/or suggest recuperation session based on this history, on the frequency of training, and on the results obtained during each test and training session. For example, the set of exercises, and the pace for each exercise, may depend on the speed of progression of each muscular parameter between successive sessions.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
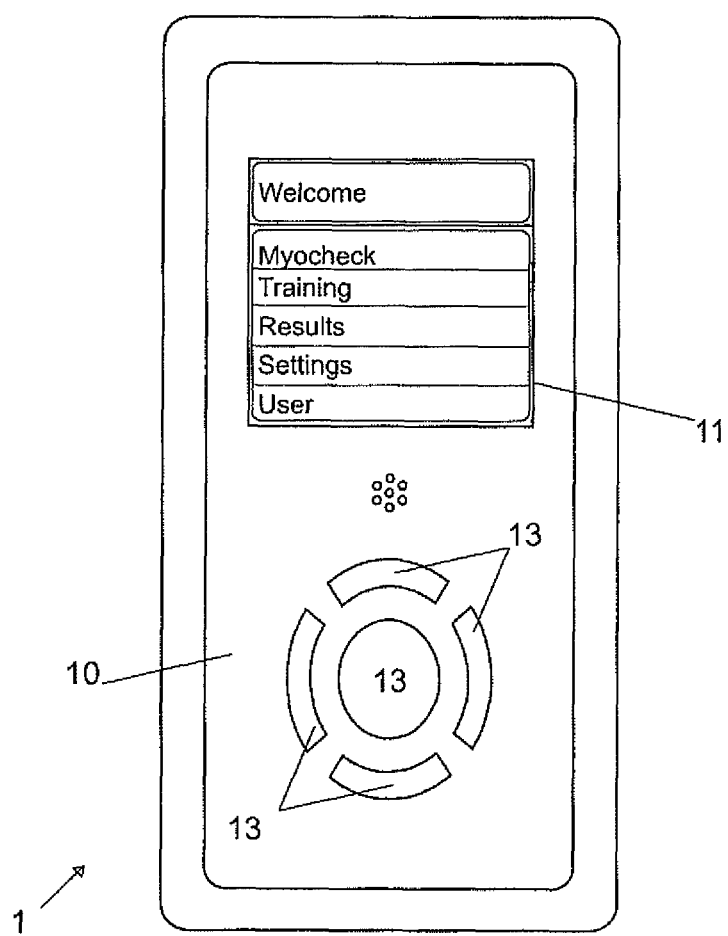
FIG. 1 illustrates a device for evaluating muscular capacity according to the invention.

An example of device according to the invention is illustrated on FIG. 1. The device 1 comprises a casing 10, for example a plastic casing weighing less than 100 grams, preferably less than 50 grams (including the contents), which the athlete can attach, depending on the exercise performed, to his hip, for example using a Velcro strip and a belt, etc. The belt allows fastening of the device close to the athlete's hips or waist.

A device integrated with a bracelet, or within a wristwatch, may also be used, although this solution is likely to produce more artefacts and to measure accelerations not due to the movements of the legs.

The device further includes a display 11, for example an alphanumeric or matrix liquid-crystal display screen, for displaying control menus, the state of the memory, the state of the battery, and also numerical quantities determined during or after the test. Control members 13, for example buttons and/or members for moving a cursor, make it possible to navigate the menus displayed, to select options to input data and to select the results displayed. In a preferred embodiment, the device has four buttons for navigating the menus, these being placed around a central confirm button.

The device preferably includes a three-axis accelerometer (not shown), for example an accelerometer made in the form of a MEMS component and linked to an analog-digital converter, or directly integrating such a converter, so as to deliver sequences of acceleration measurements along three axes. The accelerometer may have one or more preferential axes, offering greater precision, resolution and/or measurement range than in the other axes. This preferential axis will preferably be aligned vertically when the device is in its normal use position, so as to improve the measurement in the vertical direction. The measurement range of the preferential axis or axes is preferably greater than ±8G, or even ±10G. The resolution of this axis is preferably greater than 10 or even 12 bits. Preferably, the device does not contain a gyroscope, so as to reduce its cost, its consumption and the volume of data generated. The use of a one-axis gyroscope, or even a three-axis gyroscope, could however be envisioned for certain types of muscular capacity test, or for calibrating the vertical position more certainly.

The device 1 is preferably electrically autonomous, supplied for example by means of a battery or a storage battery that can be recharged, for example via an USB connection, or by removing it from the casing. The battery supplies in particular a microprocessor or a microcontroller provided with a RAM and/or EEPROM memory. The microprocessor executes a program preferably containing EEPROM, and able to be replaced via one of the interfaces, in order to analyze the measurement data delivered by the accelerometer and to control the display so as to display the desired quantities. The program stored in this memory is thus arranged for triggering the computing means to compute a plurality of muscular parameters based on a series of acceleration values, to determine a set of training exercises based on said muscular parameters, and to display said set of muscular parameters, as will be described.

The device 1 also includes a real-time clock (RTC), in particular for measuring time intervals Δt, and also a buzzer or a loudspeaker for generating alarm signals or other sounds. An input/output module (UART) is used to exchange data between the microprocessor and external devices, for example for reprogramming it or for transmitting measurement results to a personal computer, a mobile telephone or another external data processing device. The module also makes it possible to introduce, at any time, the parameters for new types of test and to determine the way in which the measurement data for these new tests will be exploited, so as to extract the desired representative quantities therefrom.

The device 1 displays the menu of FIG. 1 when it is switched on. This menu allows selection between a "Myocheck", training, display of test results, changing user's settings, and selecting another user.

The Myocheck (first option of the menu of FIG. 1) is a muscular test comprising a series of short movements for measuring and calculating muscular parameters of the athlete, especially muscular parameters of his legs and feet. The training option allows the user to make some gymnastic or training exercises, and to control the execution of those exercises with his device. The result option allows the user to display the result of previous similar tests. The settings option allows the user to enter some body parameters, such as weight and size, used for the calculation of results and for the preparation of personalized training programs. The user option allows the user to indicate his identity, especially when the device is shared by different users.

Figure 2:
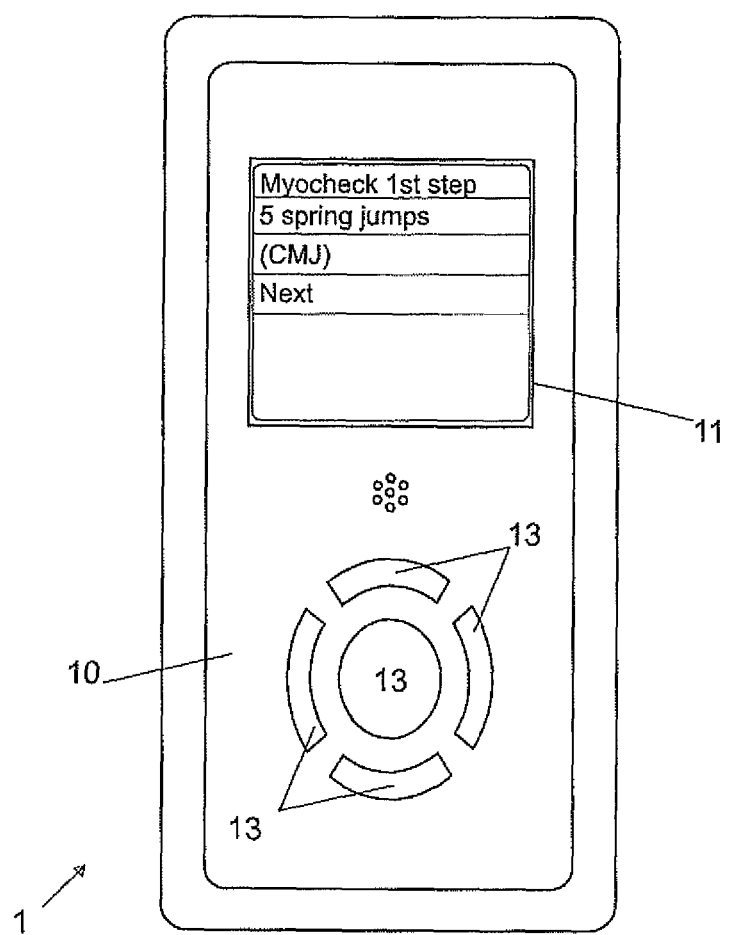
FIG. 2 illustrates the device before a first phase of a muscular test.

FIG. 2 illustrates a possible display immediately after selection of the option "Myocheck" in the menu of FIG. 1. In one embodiment, this initial muscular test comprises a first series of five spring jumps, preferably "countermovement jumps" (CMJ), followed by a series of twenty fast jumps (rebounds). Other exercises, including squat jumps, are possible. The total duration of this initial test is preferably less than 5 minutes.

Figure 3:
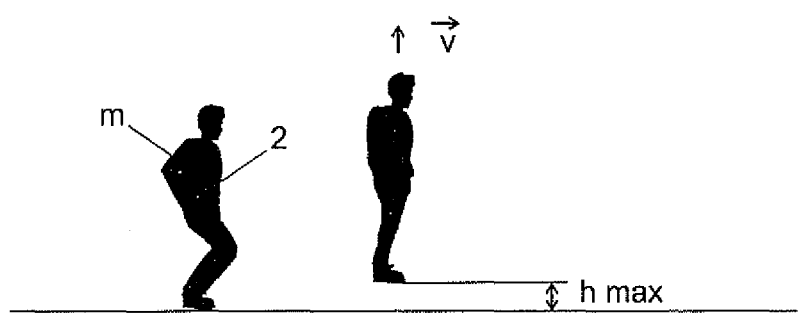
FIG. 3 illustrates a countermovement jump test.

FIG. 3 illustrates a "countermovement jump" test used as a first part of the muscular test in order to determine the force and the extension of an athlete 3. In this test, the athlete starts in a standing position (legs straight) and is permitted to perform a flexing movement before the extension and jump. In one example, the user is requested to make five separate jumps, separated by a short pause between each jump; the device emits a beep to invite the athlete to make each jump.

The muscular test preferably comprises another part immediately after the five countermovement jumps of the first part. In one embodiment, the second part of the test comprises a series of jumps (rebounds), for example 20 jumps carried out on the spot, possibly using the arms to help. This series is used in order to measure the reactivity of the athlete; it is requested to make a new spring immediately after reception of the previous spring.

Other tests may be performed as part of the initial Myocheck, such as "squat jumps", or jumps in which the athlete is permitted to swing his arms during the jump, in particular so as to check the coordination between arms and legs. Squat jump and countermovement jump tests may also be carried out with a weight on the athlete's shoulders.

Figure 4:
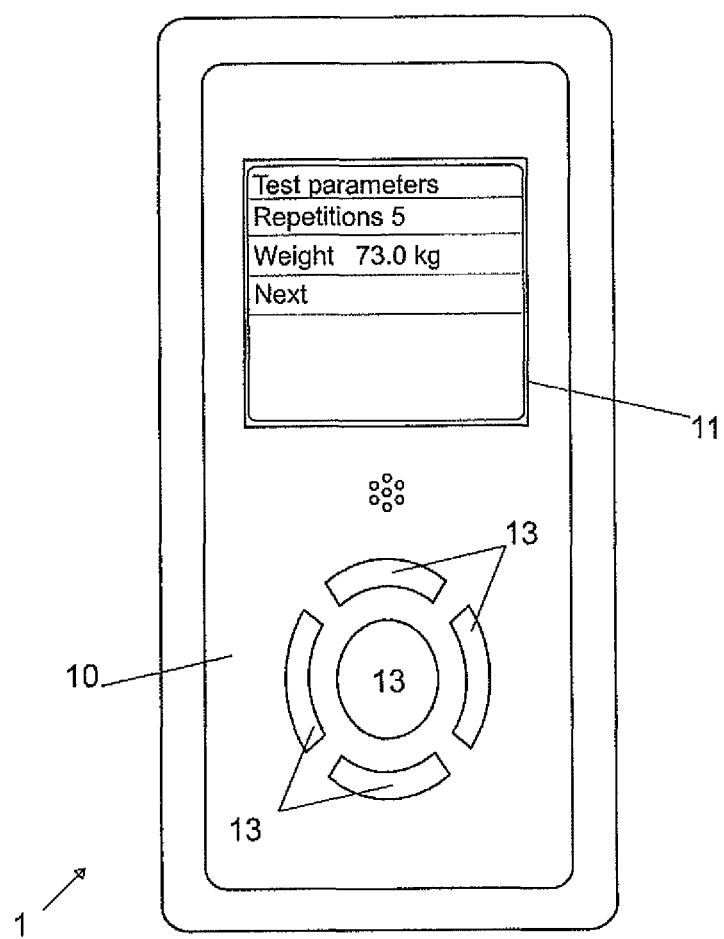
FIG. 4 illustrates the device displaying some test parameters before the first phase of the muscular test.

FIG. 4 illustrates the display of initial test parameters before execution of those five countermovement jumps, as part of the initial "Myocheck". The display repeats the number of repetitions expected, and indicates the athlete's weight as retrieved from the user's settings. The athlete needs to correct this value if it is not correct.

Figure 5:
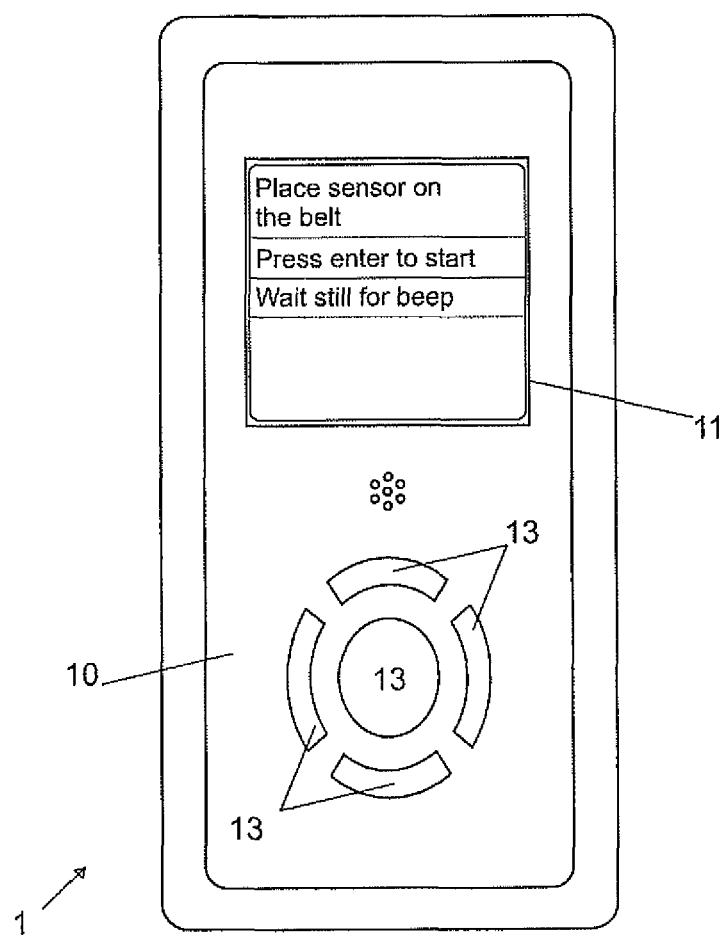
FIG. 5 illustrates the device displaying some explanation before the first phase of the muscular test.

FIG. 5 illustrates the display of recommendations on the display's device just before the initial countermovement jump test as part of the initial muscular test (Myocheck). The athlete is invited to place the device on his belt, to press the enter button, and to wait still for a beep. This still period is used by the device for determining the vertical direction (i.e., the direction of gravity acceleration), based on values delivered by the accelerometer along three axis X, Y, Z.

The device 1 emits an audio signal immediately, such as a beep, as soon as the vertical direction has been reliably found, and thus invites the athlete to perform a first countermovement jump. A series of acceleration values along this vertical axis are measured and calculated during this spring. After a short pause (for example a few seconds), a new beep is emitted, and the athlete is invited to make a new countermovement jump. This is repeated five times, for example, or more if the values measured during one jump are not reliable.

Figure 6:
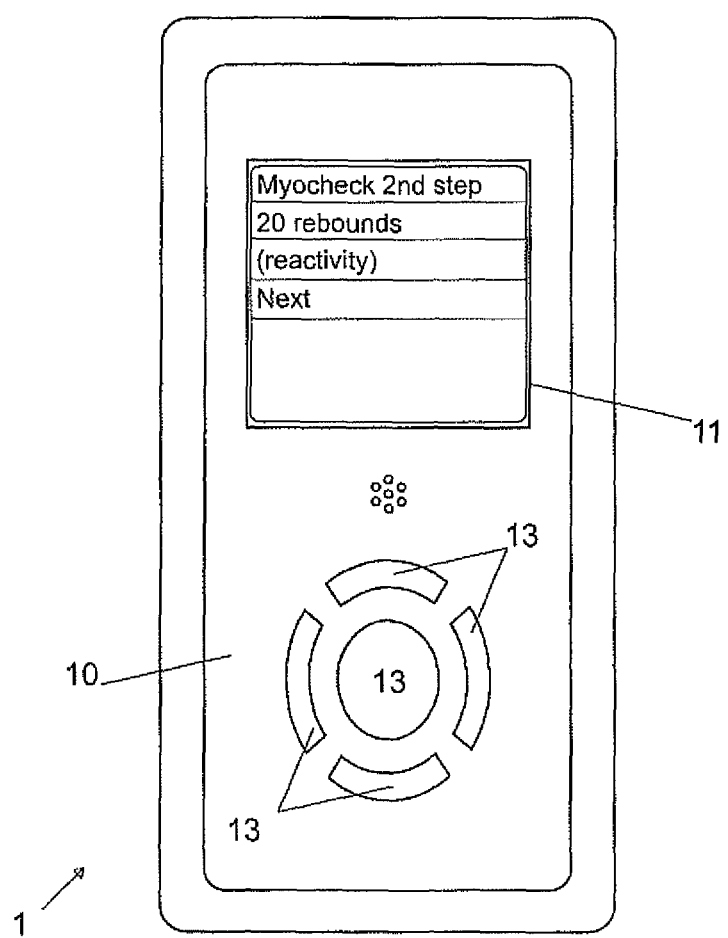
FIG. 6 illustrates the device before a second phase of a muscular test.

FIG. 6 illustrates the display of the device before the second part of the Myocheck muscular test. In this example, this second phase implies 20 rebounds, i.e. a series of 20 jumps without any pause between each jump. The athlete thus needs to jump as high as possible, and to minimize the time of the contact with the ground. This test is especially useful for determining the reactivity, the coordination and the stiffness of the athlete. A single audio signal, such as a beep, is emitted before the 20 jumps, and at the end of the test.

Figure 7:
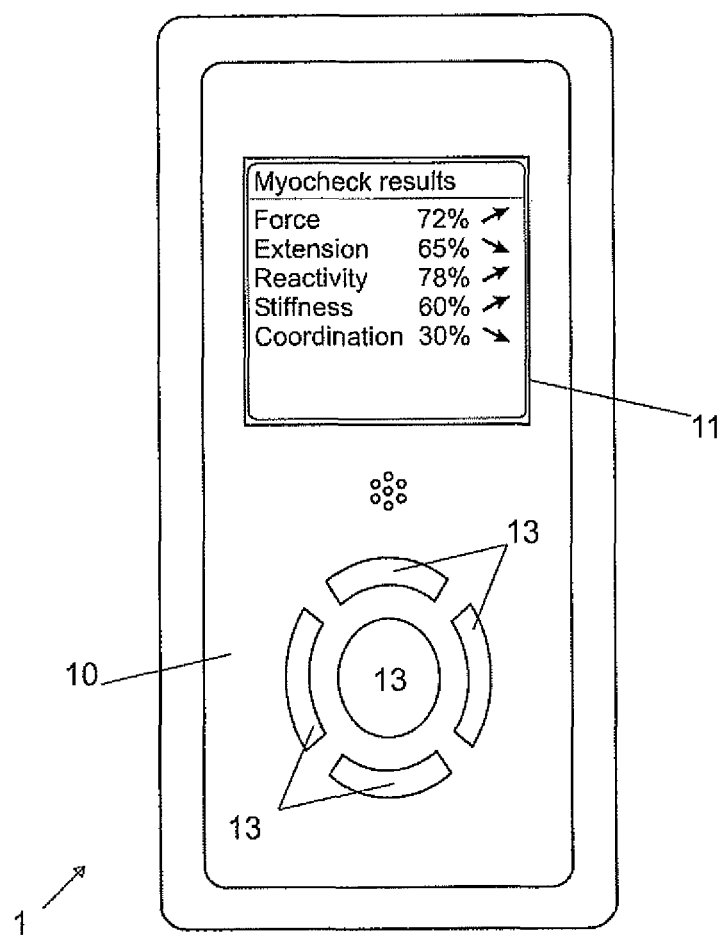
FIG. 7 illustrates the device displaying results, including muscular parameters in relative values, after the muscular test.

FIG. 7 illustrates the display of the device after the Myocheck test, for example after the rebound test. The device 1 then calculates a plurality of muscular parameters based on the series of acceleration values measured during the first and second parts of the initial Myocheck, i.e., during the countermovement jumps and during the rebound tests.

In one embodiment, those muscular parameters include:

The muscular force—retrieved for example during the countermovement jump only, and based on an average of five jumps, on the average of the three best jumps, or on the best value only;

The extension—which directly depends on the maximal or average vertical speed during the countermovement jumps;

The reactivity—measured during the rebound test, and depending on a ration between the time of flight and the time of contact with the ground;

The muscular stiffness—which depends on the height of lowering of the muscles after the contact with the ground;

The coordination—depending on the variation of reactivity between several jumps during the rebound test.

It has been found that this particular selection of parameters, which can all be retrieved and computed with the above described device 1, is useful for determining the muscular ability of an endurance athlete, such as a runner.

As most athletes probably don't know which range of absolute values for those parameters are expected, each parameter is preferably displayed in relative value, for example as a percentage of results reached by top athletes and elite runners. For example a value of 72% for the force indicates that the current user of the device has 72% of the force of a top runner. Other graduations, including qualitative marks ("excellent", "good", "satisfactory", etc), or scales based on a Gaussian distribution, may also be used.

The results preferably also include an indication of the progress made since the last test, and/or since any other starting point, such as the commencement of usage of the device. In the illustrated example, the progress is indicated by an arrow next to each muscular parameter.

Figure 8:
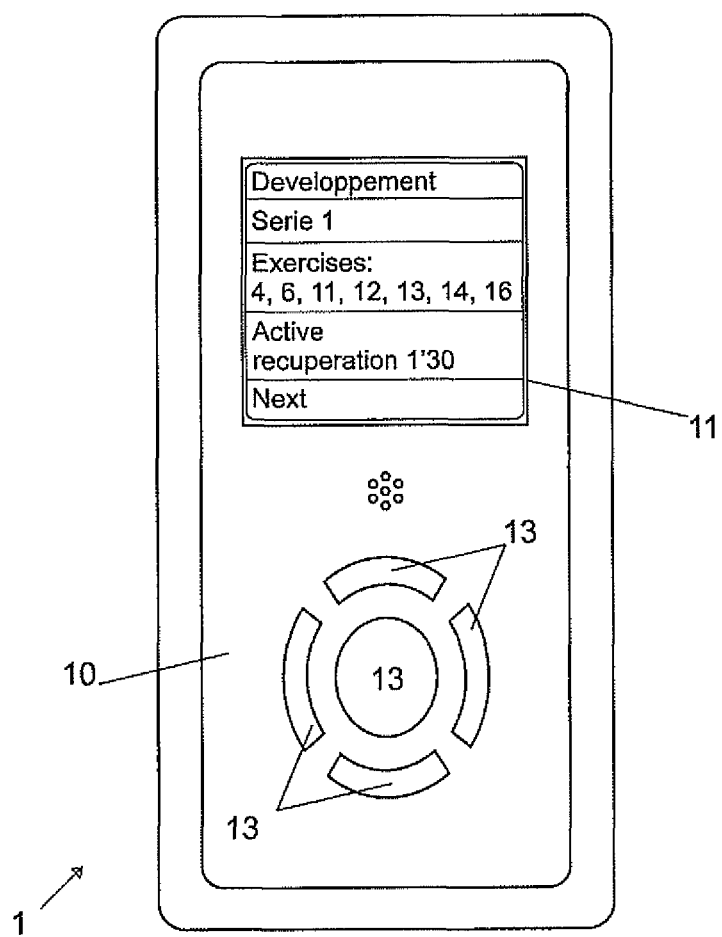
FIG. 8 illustrates the device displaying a personalized program of training exercises based on the results of the muscular test.

FIG. 8 illustrates the display of one set of training exercises personalized for the athlete, determined by a software in the device 1 and based on the muscular parameters computer after the muscular test. This set of exercise is selected for the current user among a wider catalogue of exercises; the selection depends on the results of the previous muscular test, and especially on the two weakest parameters which needs the more improvements. The aim is thus to achieve more homogeneous values for each muscular parameter.

In one embodiment, the device proposes two series with six exercises in each series. The selection of exercises, as well as the execution parameters of each exercise, depends on the two weakest parameters of the athlete, as determined during the initial test. The two series are however different in order to avoid monotony.

This selection of exercises, and the parameters of each exercise, may also depend on progress made since the last test, and/or on the whole history of tests. The aim is for example to detect overtraining and situations where repetition of a particular exercise does not improve a particular muscular parameter any more, while a longer period of recuperation may be beneficial.

Moreover, the selection of exercises, and the parameters of each exercise, depends on the phase of the training. In one preferred embodiment, the device proposes a training with three different phases:

During a first phase, which last for example from 2 to 5 weeks, the aim is to improve the general condition, in order to prevent injuries, improve the technique, etc. The aim here is to improve the general physical preparation; this phase typically includes exercises for improving abdominal and back muscles (sheathing).

During a second phase (development), which last for example from 2 to 5 weeks, the athlete is invited to develop his resistance and improve his elastic qualities.

During the third and last phase, which may last for example from 2 to 10 weeks, the user is invited to run intervals, in order to raise intensity and improve his qualities as a runner.

Thus, the set of exercises proposed to the athlete preferably depends on the training phase of the athlete; this phase may be selected by the athlete, or preferably by the device itself.

History of previously suggested or executed exercises may also be considered for this selection, as well as results of measures and calculations during those exercises. The device may thus suggest a personalized training program which depends mainly on the most current muscular test, but also on previous tests and on previous suggestions, in order to ensure a maximum of benefits. A random generator may also be used for selecting among different equivalent exercises, in order to vary the type of exercises suggested to the athlete and to make the training program more attractive and less repetitive.

Exercises are preferably indicated by an exercise's identifier, for example a number or a name; a complete description of each exercise is preferably given in a manual or DVD associated and distributed with the device. The device also suggests a personalized number of repetition for each exercise, and a duration for the recuperation after each exercise, between each type of exercise, and/or between each series of different exercises.

In the example of FIG. 8, the proposed training program is based on a series of short gymnastic exercises for improving, among other, the impulsivity, the coordination, the neuromuscular characteristics, etc of the athlete. A typical training program comprises for example two series and six different exercises in each series, wherein each exercise must be repeated for example from 5 to 20 times depending on the exercise. Again, not only the type of exercises in each series, but also the condition of execution, are determined by the device based on the result of the test. For example, the device may determine the number of jumps to do, the speed for a specific exercise, etc.

The device 1 is preferably worn and used during the execution of those recommended training exercises, and provides guidance and support for the athlete. For example, the device may indicate to the user which exercise to perform at each moment, and display or speak a description of each exercise. The speed of execution, and the duration of the pauses between the exercises, may also be defined by the device which preferably emits various audio signals in order to indicate the beginning and the end of each exercise, and help the user to perform the right exercise at the right time and pace. In one typical exercise, the device may first explain to the user that he needs to make 10 jumps, emits a first audio signal before each jump, count the number of jumps, and emit a different audio signal when the 10 jumps have been done, or in case of error.

The device may also measures acceleration during each training exercise, and verify the correct execution of each exercise. Results may be computed after each exercise, for example in a qualitative form with three levels such as "high", "average", "low", or "short", "average", "long" (for a duration etc). Incorrect execution of an exercise can also be indicated.

Those results can also be used for modifying future training plans and future lists of exercises. For example, the device can determine progress made by the athlete, or detect overtraining situations, and adapt future training programs in consequence. The list of exercises is thus defined during the initial muscular test, and iteratively adapted during execution of the exercises with the device.

Figure 9:
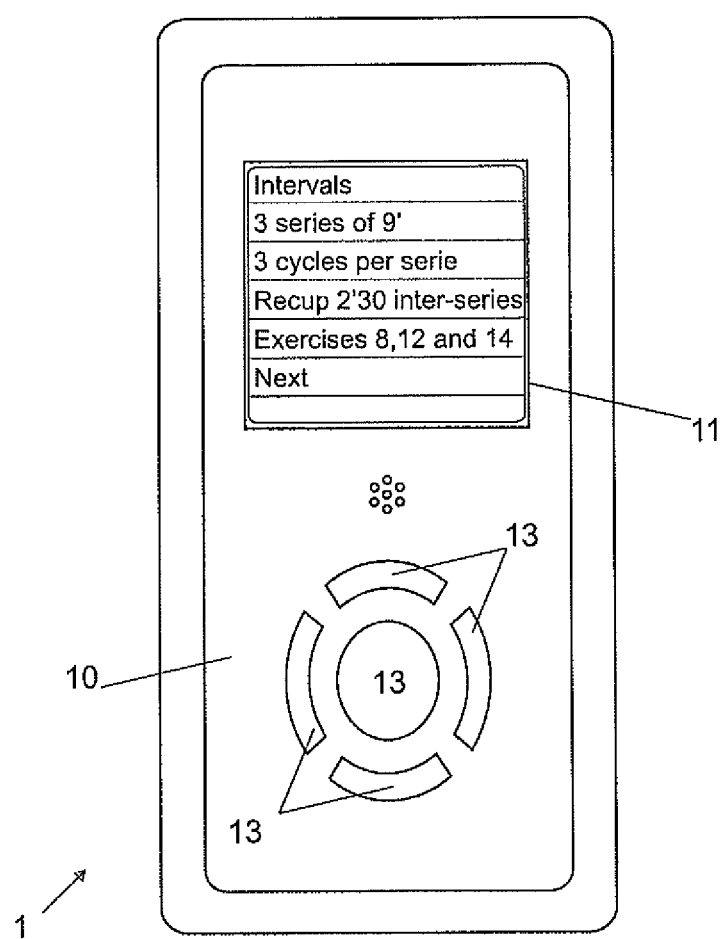
FIG. 9 illustrates the device displaying a personalized program for an interval training session based on the results of the muscular test.

FIG. 9 illustrates the display of one plan for an interval session, i.e., a running session at different paces and including different exercises selected as a function of the results of the Myocheck and of previous exercises. As for the set of exercises displayed on FIG. 8, this plan is determined by software in the device 1 and based on the muscular parameters computer after the muscular test. The interval session comprises various exercises which are selected for the current user among a wider catalogue of exercises; again, the selection depends on the results of the previous muscular test, and especially on the two weakest parameters which needs the more improvements. In the illustrated example, the device 1 suggests an interval session comprising three series of 9 minutes each, with cycles per series and a recuperation of 2 minute and 30 seconds between each series. Each series includes execution of the exercises 8, 12 and 14 among the already described catalogue of exercises.

Figure 10:
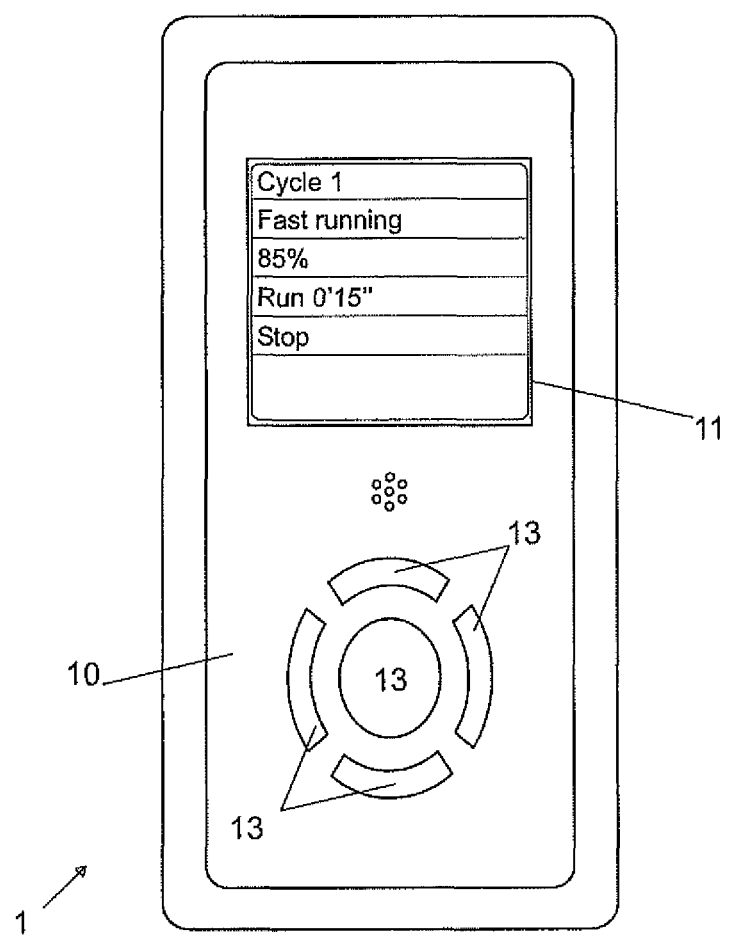
FIG. 10 illustrates the device displaying some explanation before the first series of a personalized interval session.

FIG. 10 illustrates a display proposed by the device during execution of the personalized interval session. In this example, the exercise proposed by the device 1 comprises 15 seconds of fast running at 85% of the maximal pace; the device emits a beep at the beginning and at the end of the exercise, and verifies the correct execution.

Figure 11:
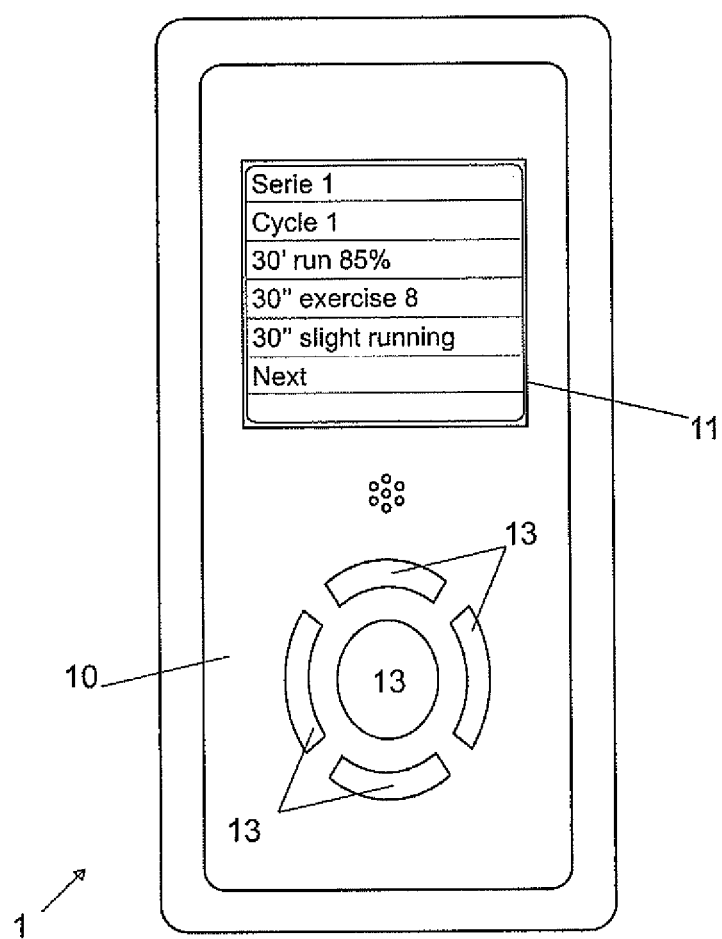
FIG. 11 illustrates the device displaying some explanation before the first cycle of the first phase of the muscular test.

FIG. 11 illustrates the display of the device at the beginning of the first cycle in an example of interval session. In this example, the cycle comprises 30 minutes run at an 85% pace, then 30 seconds of execution of exercise 8, and finally 30 minutes of slight running. Again, the device 1 is advantageously worn during this session, and presents the user with various audio and text signals in order to give him instructions, measure time, and verify correct execution of each exercise.

The invention also relates to a data carrier storing a computer program for causing a programmable device with an accelerometer to carry out the steps of any of above described methods when the program is executed.

The invention finally also relates to a method using an accelerometer for measuring, computing and displaying the reactivity and/or the coordination of an athlete.

The invention claimed is:

1. A method for optimizing training of athletes, comprising the steps of:
    during an initial test, automatically measuring with an three-axis accelerometer of a single portable device, a series of acceleration values during a series of N short movements performed by an athlete, said single portable device being arranged to generate a signal for initiating the initial test and a signal for ending the initial test;
    operating said single portable device so that it:
        calculates a plurality of muscular parameters based on said series of acceleration values, wherein said plurality of muscular parameters include at least four different muscular parameters, wherein said plurality of muscular parameters comprise extension, reactivity, muscular stiffness, and coordination,
        determines among said plurality of muscular parameters, M weakest muscular parameters of the athlete, each of the M weakest muscular parameters being different, and wherein M is a positive integer greater than one, and
        automatically selects, on the basis of said initial test and said M weakest muscular parameters, a set of training exercises personalized for said athlete, said set of training exercises comprising a personalized session of interval running, said personalized session including periods of runs at various particular paces and short gymnastic exercises between said periods,
    presenting, by a display of said single portable device, said set of training exercises to said athlete;
    executing, by the athlete, said set of training exercises;
    operating said single portable device to
        measure acceleration values during execution of the set of training exercises, so as to directly measure said plurality of muscular parameters of the athlete during the execution of said set of training exercises,
        check, during and/or after the execution of the set of training exercises, if the athlete has improved the M weakest muscular parameters, and
        use the measured acceleration values to automatically verify correct execution of said set of training exercises, by computing results after each exercise of said set of training exercises, and/or by indicating incorrect execution of an exercise of set of training exercises by audio and/or text signals,
    wherein said three-axis accelerometer comprises one or more preferential axes, offering greater precision, resolution and/or measurement range than in the other axes, and
    wherein one of the one or more preferential axes is aligned vertically when the single portable device is in its normal use position, so as to improve the measurements in the vertical direction.

2. The method of claim 1, wherein said series of N short movements comprises jumps, wherein the reactivity increases with a time of flight during jumps, and decreases with a duration of ground contact between two jumps; and wherein the coordination increases with a regularity of the reactivity measured for all jumps within said series of N short movements.

3. The method of claim 2, wherein said reactivity depends on the square of time of flight divided by the duration of ground contact, computed for each jump.

4. The method of claim 1, wherein said series of N short movements comprises jumps, said plurality of muscular parameters being parameters of legs' musculature, and said set of training exercises being intended for improving running performance.

5. The method of claim 1, wherein said plurality of muscular parameters further includes muscular force and speed.

6. The method of claim 1, further comprising a step of retrieving, from a manual, a description of said set of training exercises.

7. The method of claim 1, wherein each exercise of said set of training exercises consists of a predefined number of gymnastic exercises.

8. The method of claim 1, wherein audio and/or visual signals are given by said single portable device during the initial test and during the set of training exercises, in order to suggest a given pace of performance of the initial test and execution of the set of training exercises.

9. The method of claim 1, wherein future set of training exercises are adapted based on said measured acceleration values during execution of said set of training exercises.

10. The method of claim 1, wherein said plurality of muscular parameters are displayed, by said single portable device, after the performance of said initial test.

11. The method of claim 1, wherein said plurality of muscular parameters are displayed in relative parameters, with reference to values reached by reference athletes.

12. The method of claim 1, wherein said series of N short movements comprise a series of counter movement jumps and a series of rebounds, wherein force is calculated based on acceleration values measured during said series of counter movements jumps, wherein the reactivity and the coordination are calculated based on acceleration values measured during said series of rebounds.

13. The method of claim 1, wherein said series of N short movements comprises jumps, wherein the reactivity increases with a time of flight during jumps, and decreases with a duration of ground contact between two jumps, and the coordination increases with a regularity of the reactivity measured for all jumps within said series of N short movements, and wherein said reactivity depends on the square of time of flight divided by the duration of ground contact, computed for each jump.

14. The method of claim 1, comprising the steps of: operating said single portable device to measure said plurality of muscular parameters of the athlete during the execution of said set of training exercises at a plurality of different times, and at each of said plurality of different times, storing in a memory of said single portable device said measured plurality of muscular parameters to generate a history of measured plurality of muscular parameters, and adapting, by the single portable device, said set of training exercises based on the history of measured plurality of muscular parameters.

15. The method of claim 1, comprising the steps of: operating said single portable device to measure one or more performance-indicating parameters of the athlete during the execution of said set of training exercises at a plurality of different times, and at each of said plurality of different times, storing in a memory of said single portable device said measured one or more performance-indicating parameters to generate a history of measured one or more performance-indicating parameters, and suggesting future set of training exercises, by the single portable device, which aid recuperation, based on the history of measured one or more performance-indicating parameters and/or the number of different times which the set of training exercises have been executed.

16. The method of claim 1, comprising the step of: operating said single portable device to detect an over-training of said athlete and to adapt future set of training exercises based on said over-training.

17. The method of claim 1, further comprising the steps of: displaying on the display of said single portable device and before the initial test, recommendations to the athlete inviting the athlete to wait still for a period, and during said period, operating the single portable device to determine the vertical direction based on acceleration values measured, by the three-axis accelerometer, along all the axes of the three-axis accelerometer.

18. The method of claim 1, wherein said three-axis accelerometer is made in the form of a MEMS component and linked to an analog-digital converter, or directly integrating such a converter, so as to deliver sequences of acceleration measurements along three axes.

19. The method of claim 1, wherein the measurement range of the one or more preferential axes is greater than ±8G.

20. The method of claim 1, wherein the resolution of the preferential axis or axes is greater than 10 bits.

21. The method of claim 1, comprising the step of: selecting said set of training exercises, by a random generator, among different equivalent exercises, in order to vary the type of exercises suggested to the athlete and to make the training program more attractive and less repetitive.

22. The method of claim 1, comprising the step of: selecting said set of training exercises among a wider catalogue of exercises; the selection depending on the results of the initial test, and on two weakest muscular parameters of the M weakest muscular parameters which need more improvements.

23. The method of claim 1, comprising the step of: computing results after each exercise of the set of training exercises in a qualitative form with three levels.

* * * * *